United States Patent [19]
Watson et al.

[11] Patent Number: 5,891,617
[45] Date of Patent: Apr. 6, 1999

[54] CRYOPRESERVATION OF HARVESTED SKIN AND CULTURED SKIN OR CORNEA EQUIVALENTS BY SLOW FREEZING

[75] Inventors: Stephen Watson, Hyde Park; Mehmet Toner, Wellesley, both of Mass.

[73] Assignee: Organogenesis Inc., Canton, Mass.

[21] Appl. No.: 380,099

[22] Filed: Jan. 30, 1995

Related U.S. Application Data

[63] Continuation-in-part of Ser. No. 121,377, Sep. 15, 1993, Pat. No. 5,518,878.
[51] Int. Cl.$^6$ ...................................................... A01N 1/02
[52] U.S. Cl. ........................... 435/1.3; 435/347; 435/374; 424/571; 424/572
[58] Field of Search ........................... 435/1.3, 347, 374; 424/571, 572

[56] References Cited

U.S. PATENT DOCUMENTS

| | | | |
|---|---|---|---|
| 3,842,831 | 10/1974 | Beisang et al. | 128/155 |
| 4,485,096 | 11/1984 | Bell | 424/95 |
| 4,485,097 | 11/1984 | Bell | 424/95 |
| 4,539,716 | 9/1985 | Bell | 623/1 |
| 4,546,500 | 10/1985 | Bell | 623/1 |
| 4,580,409 | 4/1986 | Angelier et al. | 62/340 |
| 4,604,346 | 8/1986 | Bell | 435/1 |
| 4,837,379 | 6/1989 | Weinberg | 424/101 |
| 4,890,457 | 1/1990 | McNalley et al. | 62/65 |
| 5,084,377 | 1/1992 | Rowan et al. | 435/1 |
| 5,145,770 | 9/1992 | Tubo et al. | 435/1 |
| 5,298,417 | 3/1994 | Cancedda et al. | 435/240.1 |
| 5,518,878 | 5/1996 | Wilkins et al. | 435/1.3 |

FOREIGN PATENT DOCUMENTS

| | | |
|---|---|---|
| 0364306 | 4/1990 | European Pat. Off. . |

OTHER PUBLICATIONS

Rich SJ et al., "Corneal Tolerance of Vetrifiable Concentrations of Glyconol" CryoBiology 29: 153–64 (1992).
Fahy et al., "Vitrification as an Approach to Cryoprservation," Cryobiology 21:407–426 (1984).
Takahashi, et al., "Vitirification of Human Monocytes," Cryobiology, 23:103–115 (1986).
Parenteau, et al., "Epidermis Generated in Vitro: Practical Considerations and Applications," J. of Cellular Biochemistry, 45:245–251 (1991).
Parenteau, et al., "The Organotypic Culture of Human Skin Keratinocytes and Fibroblasts to Achieve form and Function," Cytotechnology, 9:163–171 (1992).
Bell, et al., "The Living Skin Equivalent: Its Organotypic Properties and Its Responses to Irritants," Toxic in Vitro, 5:591–596 (1991).
Hubel, et al., "Intercellular Ice Formation during the Freezing of Hepatocytes Cultured in a Double Collagen Gel," Biotechnology Program, 7:554–559 (1991).
Gay, et al., "The Living Skin Equivalent as a Model In Vitro for Ranking the Toxic Potential of Dermal Irritants," Toxic in Vitro, 6:303–315 (1992).
Rall, W.F., Factors Affecting the Survival of Mouse Embryos Cryopreserved by Vitrification, Cryobiology, 24:387–402 (1987).
Madden, et al., Cryobiology, vol. 30, issued 1993 "The Effect of Polyvinylpyrrolidone and the Cooling Rate during Corneal Cryopreservation", pp. 135–157.
Delbosc, et al., Journal of French Opthalmology, vol. 7, No. 4, issued 1984, "la cryoconservation corneenne chez l'homme: proposition technique originale", pp. 321–331.
Johnstone, et al., Cornea, vol. 11, No. 3, issued 1992, Cryopreservation of Rabbit and Cat Corneas at –18 to –24° C pp. 211–220.
Armitage, et al., Cryobiology, vol. 27, issued 1990, Vitrification of Organized Tissues, pp. 483–491.
May, S.R., et al., Cryobiology, vol. 17, issued 1980, "Skin Banking Methodology: An Evaluation of Package Format, Cooling and Warming Rates, and Storage Efficiency," pp. 33–45.
Teasdale, B., et al., Burns, vol. 19 (5), issued 1993, "Cryopreservation of cultured dermal fibroblast impregnated collagen gels", pp. 406–410.
Nanchahal, J., et al., Lancet, issued Jul. 22, 1989, "Cultured Composite Skin Grafts: Biological Skin Equivalents Permitting Massive Expansion," pp. 191–193.
Pegg, D.E., et al., "Ice Crystals in Tissues and Organs," *The Biophysics of Organ Cryopreservation*, pp. 117–140, edited by Pegg, D.E. and Karow, Jr., A.M., NATO ASI Series A: Life Sciences, vol. 4 (1987).

*Primary Examiner*—Sandra E. Saucier
*Attorney, Agent, or Firm*—Hale and Dorr LLP

[57] ABSTRACT

This invention is directed to cryopreservation of harvested mammalian tissues and living cultured tissue equivalents made by in vitro technology. The invention involves immersing a mammalian tissue or cultured tissue equivalent in a cryoprotectant solution, agitating the cryoprotectant solution and the immersed tissue to achieve effective penetration of the cryoprotectant solution into the tissue, and then freezing the tissue at a very slow freezing rate at 0.3° C. or less/min. In the freezing step, extracellular ice formation is initiated by seeding. The cryopreserved tissue may be stored for indefinite periods of time prior to use. The cultured tissue equivalent is an in vitro model of the equivalent human tissue, such as skin or cornea, which, when retrieved from storage can be used for transplantation or implantation in vivo or for screening compounds in vitro.

32 Claims, 13 Drawing Sheets

CRYOPRESERVATION OF HARVESTED SKIN AND CULTURED SKIN OR CORNEA EQUIVALENTS BY SLOW FREEZING

This is a continuation-in-part of application U.S. Ser. No. 08/121,377, filed on Sep. 15, 1993, now U.S. Pat. No. 5,518,878.

BACKGROUND OF THE INVENTION

1. Field of the Invention

This invention relates to the cryopreservation of both harvested tissue and cultured tissue equivalents made using in vitro technology. By use of the cryopreservation technology, either cryopreserved harvested tissue or cryopreserved cultured tissue may be stored for indefinite periods of time prior to use. The cultured tissue is an in vitro model of the equivalent human tissue, which, when retrieved from storage, can be used for transplantation or implantation, in vivo, or for screening compounds in vitro.

2. Brief Description of the Background of the Invention

In vitro technology has developed tissue equivalents for the purposes of in vitro testing or in vivo grafting for wound repair. Methods of producing such tissue equivalents are disclosed in U.S. Pat. Nos. 4,485,096, 4,604,346, 4,835,102 and 5,374,515 and are incorporated herein by reference.

The shelf life of living tissues is limited and, subsequently, their window of use is short, resulting in much waste. There is a need to preserve such tissues for extended periods of time, as in shipping and storage, until their use. The development of a cryopreservation method would extend the window of use indefinitely, ease shipping and allow for the maintenance of an inventory. To enable an inventory of tissue at burn care centers and hospitals is also desirable. Other advantages are that samples can be retained from different stages of the manufacturing cycle for quality control archives and larger production batches can be made as they can be maintained in a frozen state.

Currently, the storage time of biological materials is extended by cooling to "cryogenic" temperatures. The transition from the liquid into the solid state by lowering the temperature of the system can take place either as crystallization (ice), involving an orderly arrangement of water molecules, or as vitrification or amorphization (glass formation), in the absence of such an orderly arrangement of crystalline phase. The challenge for a cryobiologist is to bring cells to cryogenic temperatures and then return them to physiological conditions without injuring them.

There are two basic approaches to cryopreservation of cells and tissues: freeze-thaw and vitrification. In freeze-thaw techniques, the extracellular solution is frozen (i.e., in crystalline form), but steps are taken to minimize the intracellular ice formation. In vitrification procedures, there is an attempt to prevent ice formation throughout the entire sample. The former approach is problematic in that if ice crystals are formed inside the cells, they are detrimental to cell viability upon thawing. However, cells could survive a freeze-thaw cycle if they are cooled at controlled rates in the presence of non-toxic levels of cryoprotectants. The latter approach of vitrification seeks to avoid potentially damaging affects of intra- and extracellular ice by depressing ice formation using very high concentrations of solutes and/or polymers. However, the cell damage may occur to long exposure to toxic levels of these additives required for vitrification.

Cryoprotectants protect living cells from the stresses involved in the freezing process. One way cryoprotectants protect cells is by diluting the salt that becomes increasingly concentrated in the unfrozen solution as water is transformed to ice. The amount of ice is dictated by the temperature and initial composition of the solution; whereas the amount of unfrozen fraction is a function of temperature only. Cryoprotectants have several other functions. An important one is that they usually reduce the intracellular ice formation temperatures. Another function is that they stabilize membranes and proteins.

All solutions will supercool below their freezing point until they find a random nucleation site for crystal formation. When cryopreserving by a freeze-thaw method, ice formation in the extracellular medium should be deliberately initiated by seeding at low degrees of supercooling. If ice formation is not induced by seeding, ice will form spontaneously when the solution is cooled sufficiently far below its equilibrium freezing point. Because this process is random in nature, ice formation will occur at random, unpredictable temperatures; consequently, survival rates will be highly variable between repeated trials with the same freezing protocol. Furthermore, the extremely rapid crystallization which results when ice forms in a highly supercooled solution can cause damage to cells and tissues. Moreover, it has been shown that if extracellular ice formation is initiated at high degrees of supercooling, the probability of intracellular ice formation is drastically increased. This phenomenon results from the delayed onset of freeze-induced cell dehydration, which results in increased retention of intracellular water, and thus higher likelihood of ice formation in the cell.

Once the extracellular ice is seeded and the sample is surrounded by the ice phase, it is necessary to cool the sample to a cryopreserved state. The cooling step is one of the most critical steps in a freeze-thaw protocol. Due to the formation of ice, i.e., pure water, the partially frozen extracellular solution is more concentrated than the intracellular compartment. As a consequence, the cell will dehydrate by losing water in an attempt to restore thermodynamic equilibrium. As the system cools, more extracellular ice is generated and the concentration of solutes rises and forces the cells to dehydrate further. There are three characteristics of the cells that control their rate of dehydration. One is the cell membrane water permeability; the lower the water permeability, the longer it takes for the cells to dehydrate. Another is the temperature dependence of the cell membrane water permeability; all cells decrease their water permeability with decreasing temperatures. The final is cell size; larger cells take longer to dehydrate than smaller cells. Given that each cell type may have drastically different characteristics, the optimal cryopreservation conditions can vary by orders of magnitude for different cell types.

Although the exact mechanisms of cell damage during cryopreservation has not yet been completely elucidated, characteristic survival signatures generated by measuring cell survival as a function of cooling rate appear to be qualitatively similar for all cell types and displays an inverted U shaped curve. Cell survival is low at very slow and very fast cooling rates, and there is an intermediate cooling rate yielding optimal survival. Even though the optimal cooling rate and the width of the curve can vary drastically for different cell types, the qualitative behavior appears to be universal. Faster cooling rates do not allow cells enough time to dehydrate and cells form ice internally. Cell injury at fast cooling rates is attributed to intracellular ice formation. At slow rates of cooling, cell injury is thought to be due to the effects of exposure to highly concentrated intra- and extracellular salt and cryoprotectant solutions or to the mechanical interactions between cells and the extracellular ice.

It is necessary to dehydrate the cells as much as possible before they cross the intracellular ice nucleation curve. It is at this point that practically all water remaining in the cell will nucleate and form ice. It is impractical to determine the exact temperature where this will happen but it is approximately −40° C. to −50° C. when the cells are slowly frozen in the presence of 1M to 2M concentrations of cryoprotectants. It is important to note that the amount of water that turns to ice inside a cell at this point may be innocuous when frozen, but if not thawed fast enough, it will expand and kill the cell upon thawing. (*The Biophysics of Organ Cryopreservation*, Pg. 117–140, edited by David E. Pegg and Armand M. Karow, Jr. NATO ASI Series A: Life Sciences Vol. 147 1987 Plenum Press, New York 233 Spring St., New York, N.Y. 10013).

Before the development of a commercially viable skin equivalent, cadaver skin was used for the purposes of grafting. Cryopreservation protocols were developed so that burn centers and hospitals could maintain skin banks. A number of different protocols were developed utilizing different cryoprotectants, freeze rates, packaging formats and storage conditions. Most researchers agreed upon a fast thaw protocol. The success or failure of the protocol was measured either by graft take to a wound bed or by cell viability assay.

In U.S. Pat. No. 3,842,831 to Beisang is disclosed a method for the cryopreservation of cadaver skin patches. The method involves the attachment of the cadaver skin to a loosely woven scrim or backing and, together, the skin patches and the scrim are rolled prior to freezing. No cryoprotectant is employed, though the inventors suggest the use of either glycerin or DMSO. The freezing protocol employs a fast uncontrolled (fixed temperature) freeze rate protocol to a cryogenic temperature of −70° C.

May S R and F A DeClement, *Skin Banking Methodology*, 17, 33–45 (1980), performed an evaluation of packaging geometry and cooling and warming rates using dermatome cadaver skin. The results suggested that cadaver skin be flat, rather than rolled, and that a slower controlled rate of freezing be employed.

U.S. Pat. No. 5,145,770 to Tubo discloses a cryopreservation method for keratinocyte sheets that employs a cryoprotectant of a non-cell penetrating agent, such as dextran, and a cell penetrating reagent, such as glycerol, with a cooling rate of about −1° C./minute. Similarly, EP 0 364 306 to Chao et al, discloses a method for cryopreserving a sheet of living, cultured epithelial cells but utilizing both DMSO and glycerol as a cryoprotectant and a freezing protocol of preferably −1° C./minute.

U.S. Pat. No. 5,298,417 to Cancedda et al, discloses a cryopreservation protocol developed for single layer constructs such as epithelial sheets prepared as described in U.S. Pat. Nos. 4,016,036, 4,304,866 and 4,456,687. Epidermal sheets were incubated with a cryoprotectant of either 8–15% glycerol or DMSO and were cryopreserved by employing a controlled rate protocol where the cooling rate is slower at the start than at the end of the protocol and is characterized by an increase in temperature before the culmination of the freezing procedure.

A method for the cryoprotection of dermal fibroblasts in a collagen gel was investigated by Teasdale et al, *Burns*, 19 (5) 406–410 (1993). Teasdale determined that optimum cell viability could be obtained by freezing at −0.5° C./minute with DMSO as a cryoprotectant.

Nanchahal et al., "Cultured composite skin grafts: Biological skin equivalents permitting massive expansion," *The Lancet*, 2 (8565), 191–193 (Jul. 22, 1989), discusses a technique for storage of composite cultured tissue grafts utilizing a cryoprotectant of 15% glycerol and 10% FCS in Medium 199. The grafts and the cryoprotectant, were incubated at 37° C. for two hours and were then frozen at −1° C. per minute to −70° C. and then stored in liquid nitrogen. After fast thawing of the grafts, their viability was determined by culturing for two weeks and by grafting to hairless mice. A final evaluation was made by grafting to three patients undergoing tattoo excision.

Johnstone et al. "Cryopreservation of Rabbit and Cat Corneas at −18° to −24° C.," *Cornea*, 11(3): 211–220 (1992), is directed to a simple procedure for cryopreservation of rabbit and cat corneas which utilizes a domestic freezer rather than liquid nitrogen or very low temperature freezers. Perfusion of cryopreservative is obtained by placing corneas in successive solutions of 50% fetal calf serum and McCarey-Kaufman medium with increasing glycerol and glucose content.

Using prior art methods, it is not possible to cryopreserve cultured tissue equivalents, in part because they are relatively thick and of heterogeneous cell layers. One of the functions of these tissues in vivo are to provide a permeability barrier. Tissue functions have to be considered in the development of a cryopreservation protocol. The present inventors have discovered a method for cryopreservation that is applicable to a number of cultured tissue equivalents and to mammalian skin, one that is a surprisingly effective and commercially practical method of cryopreservation.

SUMMARY OF THE INVENTION

The present invention provides a method for the successful preservation of cultured tissue equivalents at very low temperatures which avoids the formation of intracellular ice crystals, minimizes the effective concentration of potentially harmful chemicals, and permits the rapid introduction and removal of cryoprotectants at feasible temperatures using programmable freezing equipment.

The inventors have discovered a method for cryopreserving cultured tissue equivalents made from in vitro techniques so that the tissues maintain their viability and utility as equivalents of human tissues. The invention includes the use of agitation to enhance the penetration of an effective amount of cryoprotectant. The present method provides for the cryopreservation of both harvested tissue and cultured tissue equivalents in a manner which protects structural integrity and cellular viability.

The method of this invention involves the following steps:

1) The harvested tissue or cultured tissue equivalent is immersed in a cryoprotectant solution and the cryoprotectant solution and the immersed tissue are agitated to achieve effective penetration of the cryoprotectant solution into the tissue (perfusion of the tissue); and, 2) After the perfusion of the cryoprotectant solution into the tissue, extracellular ice is seeded and the perfused tissue is cooled to a cryopreserved state by freezing the tissue at a slow freezing rate to a temperature at or below at least about −70° C., more preferably at or below −120° C., even more preferably at −140° C. and most preferably, at −196° C.

Once frozen, the cryopreserved tissue can be stored for indefinite time periods at a temperature of −196° C., the temperature of liquid nitrogen.

Thawing the cryopreserved tissue is accomplished by warming the frozen tissue at a high rate, which is done in about 1 to 3 minutes. The frozen tissue may be thawed by direct application of warmed culture media or physiologic buffered solution or by another rapid heating method.

Prior to use as an equivalent for human tissue, for grafting or in vitro testing, the thawed cultured tissue equivalent is rinsed to remove the cryoprotectant solution. The cryoprotectant solution may be removed by rinsing with, for example, an isotonic buffer solution at physiological pH. The cultured tissue equivalents can then be stored temporarily in such a buffer solution or recultured in an appropriate cell medium before use.

BRIEF DESCRIPTION OF THE FIGURES

FIG. 6A shows control non-cryopreserved Graftskin skin grafted to an athymic mouse for 14 days. (Mag=1.3×). FIG. 6B shows cryopreserved/thawed Graftskin skin grafted to an athymic mouse for 14 days. (Mag=1.3×). FIG. 6C shows hemotoxylin and Eosin stained histology section of control non-cryopreserved Graftskin graft, 14 days post graft. (Mag.=328×). FIG. 6D shows hemotoxylin and Eosin stained histology section of cryopreserved/thawed Graftskin graft, 14 days post graft. (Mag.=328×).

FIG. 7A shows control non-cryopreserved mouse skin grafted back to the animal for 30 days. (Mag=1.3×). FIG. 7B shows cryopreserved mouse skin grafted to mouse for 30 days. (Mag=1.3×). FIG. 7C shows hemotoxylin and Eosin stained histology section of the control mouse skin graft, 30 days post graft. (Mag.=131×). FIG. 7D shows hemotoxylin and Eosin stained histology section of cryopreserved mouse skin graft, 30 days post graft. (Mag.=131×).

DETAILED DESCRIPTION OF THE INVENTION

Figure 1A:
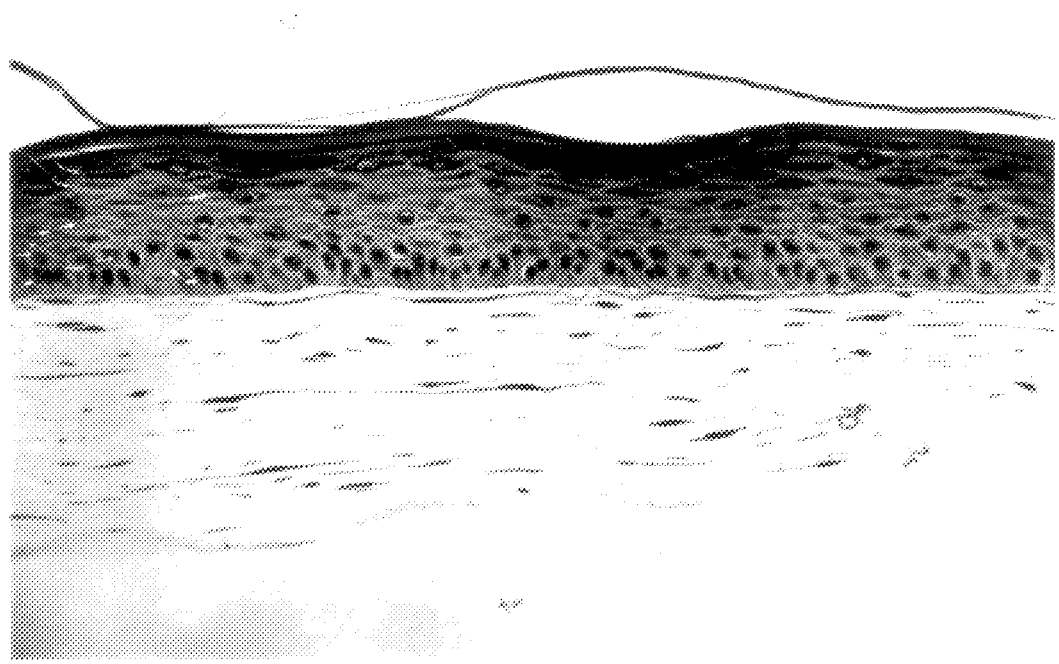
FIGS. 1A–1B show photomicrographs of non-cryopreserved LSE (1A) and cryopreserved LSE (1B) of Example 1. The four basic features of LSE: the collagen lattice with fibroblasts, the basal layer of the epidermis, the suprabasal layers of the epidermis and the stratum corneum of the epidermis of the LSE in FIG. 1B are all preserved by this method. All layers are intact and the overall morphology of cryopreserved LSE is identical to that of non-cryopreserved LSE.

Tissue engineering is an emerging area which utilizes cultured tissue cells to construct tissue equivalents which can be used to examine the response to injury by chemical agents or pharmaceutical compounds. The cultured tissue may also be used to form graftable human tissue.

Tissue equivalents have been described extensively in many patents, including U.S. Pat. Nos. 4,485,096; 4,485,097; 4,539,716; 4,546,500; 4,604,346; 4,837,379; and 5,374,515, all of which are incorporated herein by reference. One successful application of the tissue equivalent is called the "Living Skin Equivalent," which has a morphology similar to actual human skin. The Living Skin Equivalent (LSE) is composed of two layers: the upper portion is made of differentiated and stratified human epidermal keratinocytes that cover a lower layer of human dermal fibroblasts in a collagen matrix. Parenteau, et al., "Epidermis Generated In Vitro: Practical Considerations and Applications," *J. of Cellular Biochemistry*, 45:245–251 (1991); Parenteau, et al., "The organotypic culture of human skin keratinocytes and fibroblasts to achieve form and function," *Cytotechnology*, 9:163–171 (1992); and Bell et al., "The Living Skin Equivalent: Its Manufacture, Its Organotypic Properties and Its Responses to Irritants," *Toxic. in Vitro*, 5:591–596 (1991). LSE for grafting is under investigation in clinical trials for indications relating to partial and full thickness skin wounds: excision surgery, burns, venous stasis ulcers, diabetic ulcers, decubitus ulcers, and chronic inflammatory ulcers. The LSE is a full-thickness, bilayered, in vitro engineered skin tissue.

An in vitro organ equivalent of the cornea of the eye has been developed as described in U.S. Pat. No. 5,374,515, incorporated herein by reference. The cornea tissue equivalent has three distinct cell layers, the external layer, a stratified squamous epithelium, the middle layer of collagen fibers and stromal cells, and an inner layer, simple squamous epithelium, also called the corneal endothelium. An in vitro cornea equivalent can be used for in vitro toxicity assays to serve as accurate and inexpensive non-animal predictive models of in vivo ocular and dermal irritation potential for many types of products and raw materials.

The goal of cryopreservation is to preserve the structural integrity and viability of biological materials for an indefinite period of time so that these materials can be available and used as needed. Complex tissues of finite life span will require cryopreservation to expand product availability and utility. The history of cryopreservation of biological material, however, has shown that the optimization of a cryopreservation protocol for a particular cell does not necessarily give good results when used with another cell type or with other cells in a tissue. The development of more specialized methods due to the differences in cell density, water content and level of structural organization of the full-thickness LSE was required. The cryopreservation protocols of this invention are surprisingly applicable to the single layer epidermal and dermal layers alone, trilayered cornea equivalent and mammalian skin.

I. Definitions

As used herein, the term "cultured tissue equivalents" means tissue equivalents of mammalian tissues, wherein the tissue equivalents are made by in vitro techniques and are meant to include monolayer skin equivalents, either a dermal equivalent or an epidermal sheet; bilayered skin equivalents, particularly LSE; and trilayered cornea equivalents and skin equivalents. The morphology of the cultured tissue equivalents are similar to the in vivo mammalian organ, typically the human organ. For illustration, the morphology of the LSE bears many similarities to human skin. Metabolically and mitotically active human dermal fibroblasts (HDF) are found throughout the dermal layer of the construct, and have been shown to secrete collagen and other matrix components into the lattice. The epidermis consists of a basal layer shown to divide with a mitotic rate similar to that of human skin. The suprabasal epidermis shows the same strata as skin in vivo, with well defined spinous and granular layers containing keratohyalin and lamellar granules covered by a stratum corneum. Immunohistochemistry demonstrates the presence of extracellular matrix components routinely found at the dermo-epidermal junction in normal human skin, such as laminin, Type IV collagen and kalanin (GB3).

By the terminology "cryoprotectant solution" is intended any solutions which include "cell penetrating glass forming agents" or "non-cell penetrating glass forming agents" or both. The cell penetrating glass forming agent is preferably glycerol, but may include propylene glycol, ethylene glycol, dimethylsulfoxide, and other penetrating glass forming agents known in the art. Non-cell penetrating glass forming agents include high molecular weight forms of complex carbohydrates, such as chondroitin sulfate, polyvinylpyrrolidone, polyethylene glycol or hetastarch, such as hydroxyethyl starch. The cell penetrating glass forming agents or non-cell penetrating glass forming agents are diluted in a base of a physiological pH. The base is preferably DMEM, but may be substituted with phosphate buffered saline, IDMEM, MEM, M199, RPMI 1640, Ham's F-12 Ham's F-10, NCTC 109, NCTC 135, or combinations thereof. The preferred cryoprotectant solution contains 1.5M to 2.5M glycerol, preferably 2M glycerol, in a base of Dulbecco's Modified Eagle's Medium (DMEM). These solutions can be modified and optimized by one of skill in the art using known cryoprotectants and freezing, storing, thawing, and rinsing procedures that are compatible with maintaining maximal viability, depending on the particular application.

By use of the term "agitation" is meant any mechanical means of agitation to enhance perfusion of the cryoprotectant solution to achieve effective penetration of the solution into the tissue equivalent. The preferred means of agitation is shaking on an orbital shaker platform. Other means that may be employed are centrifugation, rocking platform, perfusion by means of a pump. Other methods of enhanced perfusion that would achieve effective penetration of the cryoprotectant solution into the tissue equivalent can be contemplated and employed by the skilled artisan.

A "gassed environment" is defined as an environment that prevents degassing of the sodium bicarbonate buffered base media component of the cryoprotectant solution. Over the period of time in which it takes to perfuse the tissue, these base media require the gassed environment to maintain proper pH of the cryoprotectant solution. In the present invention, $CO_2$ in air is used preferably at or about 5%, most preferably at or about 10%. The regulation of the pH of the cryoprotectant solution enables optimal cell viability.

A slow freezing rate is defined as a rate of cooling that is about or less than $-0.3°$ C. per minute, more preferably about or less than $-0.2°$ C. per minute, and most preferably about $-0.1°$ C. per minute.

Ice seeding is defined as a method of initiating ice formation to the extracellular cryoprotectant. The preferred method of ice seeding is by contacting the tray containing the tissue with a chilled probe. Alternatively, the contact may be made directly to the cryoprotectant. Ice formation can be initiated by a chamber spike where the temperature of the chamber is lowered and raised within a range sufficient to form an ice crystal. Another method would be by introducing expanding gasses such as freon or $CO_2$ to either the outside of the package or in contact with the cryoprotectant solution. Other methods of ice seeding known in the art may be substituted.

II. Cryopreservation

The present invention requires that the immersion of the harvested tissue or cultured tissue equivalent in cryoprotectant solution for a period of time under conditions sufficient to permit the perfusion of cryoprotectant in the cells of the tissue or cultured tissue equivalent. This method of cryopreservation allows for tissue to be slowly frozen and stored at or below $-70°$ C. Tissues cryopreserved by this method are stable to fluctuations in temperature between $-70°$ to $-196°$ C. Short term storage is possible at $-76°$ C., the temperature of dry ice, for transport and shipping. It is more preferable to freeze tissues to a temperature at or below $-120°$ C., the glass transition temperature of water. It is even more preferable to freeze tissues to a temperature at or below $-140°$ C., a temperature approaching the temperature of a liquid nitrogen. It is the most preferable to freeze tissues to a temperature at or below $-196°$ C., the temperature of liquid nitrogen.

The tissue that may used in the disclosed techniques can include a full thickness skin equivalent such as those disclosed in U.S. Pat. Nos. 4,485,096; 4,604,346; 4,835,102; and 5,374,515 or those disclosed in U.S. Pat. Nos. 4,963,489; 5,032,508; and 5,266,480, all incorporated herein by reference, or any cultured epidermal sheet, any cultured dermal equivalent, a cultured cornea equivalent, or harvested mammalian skin.

The method of this invention will now be described using Living Skin Equivalent (LSE) as an illustration. It will be understood by those of skill in the art that modifications can be made to the described method and still be within the scope of this invention.

The method of perfusing LSE with a cryoprotectant solution is to submerge LSE and its attached transwell in a volume of cryoprotectant solution sufficient to submerge the sample and to have equal volume of cryoprotectant solution above and below the tissue equivalent. Equal volumes allow for the uniform conduction of heat away from the tissue equivalent during cooling. In the best mode of the invention, 25 mL of 2M Glycerol in DMEM is added to a 100 mm petri dish containing the LSE and the transwell for a period of time sufficient to completely perfuse the sample, preferably between one and two hours, but most preferably for about one hour. Extended periods of time in cryoprotectant solution result in reduced cell viability in the tissue, while too short of a time does not ensure complete permeation of cryoprotectant into the tissue. Monolayer constructs will typically require less time for perfusion as they have fewer cell layers and a reduced barrier function. During this hour, penetration of cryoprotectant solution is enhanced by agitating the sample and cryoprotectant solution, typically by shaking the petri dish on an orbital platform shaker (Bellco orbital shaker) at 70 rpm in a 10% $CO_2$ gassed chamber. The 10% $CO_2$ environment, the same as the culture environment in which the LSE was fabricated, prevents the media from degassing, thus maintaining the pH of the base media component of the cryoprotectant. Agitation allows for a faster and a more complete perfusion of cryoprotectant into the tissue equivalent and better reproducibility of results between frozen LSE units. One is able to substitute an orbital shaker with an apparatus that performs an agitative motion in other spatial planes. Additionally, other methods of mechanically enhanced perfusion include, but are not limited to, rocking the construct with cryoprotectant in a vessel on a platform or centrifugation of the construct with cryoprotectant and perfusing cryoprotectant around the construct using a pump. After the LSE is perfused, the petri dish containing the LSE unit and cryoprotectant media (2M Glycerol in DMEM) is placed in a bag and vacuum sealed (Audiovac vacuum sealer 5 second vacuum and 3.9 second seal time).

Packaged LSE units are then placed into a programmable freezer (Planer) set at a starting temperature of 20.0° C. LSE units are cooled at −10.0° C./minute to −6.0° C., and are allowed to hold for 20 minutes for the purpose of equilibrating the tissue equivalent to −6.0° C., the temperature necessary for seeding ice in the cryoprotectant. Any cooling rate may be used to obtain the seeding temperature. The hold time of 20 minutes is sufficient to ensure thermal equilibration, while at least 15 minutes is typically needed. After the 20 minute hold, extracellular ice is initiated by contact of the outside of the bag containing the unit with a liquid nitrogen chilled (−196° C.) probe. The contact site must be below the level of the cryoprotectant freeze media in the bag. After all LSE units are seeded with ice crystals, the units are held an additional 5 minutes to allow the chamber to readjust to −6.0° C., as the units were opened to manually seed the ice. Cooling is then resumed at a rate of −1.0° C./minute to −8.0° C. The temperature is held at −8.0° C., for 30 minutes to allow for physical and biological equilibration of the cryoprotectant in and around the LSE before it is cooled to −70° C. Physical equilibration occurs between the liquid and ice phases of the cryoprotectant solution at a given temperature and cryoprotectant concentration and would occur in the absence of a harvested tissue or tissue equivalent. In the presence of the tissue equivalent, phase equilibration is the extracellular ice formation that occurs in the cryoprotectant solution. The biological equilibration is the equilibration that occurs between the concentration of cryoprotectant inside and outside the cells. The biological equilibration is regulated by the permeability properties of the cells and such equilibration may not be complete. During the phase change from liquid to solid, heat is liberated that would affect the cooling rate of LSE if this hold were not allowed. LSE units are then cooled preferably at −0.3° C./minute; more preferably at −0.2° C./minute; and most preferably at −0.1° C./minute to a final temperature preferably at least or below −70.0° C.; more preferably at −120° C.; even more preferably at −140° C.; or most preferably at −196.0° C. As the final freezing temperature approaches the glass transition temperature of water, −120.0° C., the less likely there will be detrimental temperature fluctuations during transfers to final storage locations.

Cryopreserved LSE was transferred from the freezer to storage preferably at −196° C. until use.

III. Thawing the Frozen Cryopreserved Cultured Tissue Equivalent

The frozen LSE tissue equivalent is thawed by rapidly warming such that the tissue is thawed in about from 1 to 3 minutes. Suitable methods for warming frozen harvested tissue or tissue equivalents at a high thawing rate, include warming using a water bath or warming using induction heating. Preferably, the frozen tissue or tissue equivalent is thawed by direct addition of culture media, warmed to 37° C., to the surface of the cryopreserved tissue.

Due to the toxic nature of the cryoprotectant agents, the cryoprotectant solution is removed from the thawed tissue or tissue equivalent within about 15 minutes after thawing, preferably as soon as possible after thawing, to avoid damaging the viability of the tissue or tissue equivalent. Once the tissue or tissue equivalent is thawed, the cryoprotectant solution is replaced with an isotonic buffer solution at physiological pH (about 6.8 to 7.4 pH).

For illustration, the cryopreserved LSE is stored in a sterile petri dish. To thaw the cryopreserved LSE, the cryopreserved LSE is removed from storage and the outer bag is cut off the petri dish. The lid of the dish is removed and 40 mL of warmed (37° C.) DMEM, the amount that will fit into the petri dish, is aseptically poured into the dish. The temperature should not be any warmer than 37° C. as the viability of sample will be endangered. After 45 seconds all liquid is removed from the dish and an additional 40 mL aliquot is added to the dish for two minutes. Using sterile forceps, the LSE unit and attached transwell is transferred to a new petri dish with 25 mL, or a volume sufficient to submerge the sample, of DMEM for 30 minutes. The media is exchanged one time for an additional 30 minutes.

A cultured tissue equivalent prepared as disclosed above may be used for transplantation or implantation in vivo or for screening compounds in vitro.

The following examples further describe the materials and methods used in carrying out the invention. The examples are not intended to limit the invention in any manner.

EXAMPLES

Example 1

Cryopreservation of Living Skin Equivalent (LSE)

Living Skin Equivalent (LSE) constructs and attached 75 mm transwell inserts (Costar), 9 to 10 days post air lift, were placed in 100 mm petri dishes (Costar). LSE constructs were perfused with cryoprotectant by submerging the constructs and the transwell with 25 mL of cryoprotective media, 2M Glycerol in DMEM, in the 100 mm petri dish for one hour. This method was improved upon by shaking the petri dish for one hour on an orbital shaker (Bellco) at 70 rpm in a 10% $CO_2$ gassed chamber. Shaking allows for a more complete perfusion and better reproducibility when frozen. After LSE was perfused, the petri dish containing LSE, transwell and extracellular freezing media (2M Glycerol and DMEM) are placed in a bag and vacuum sealed (Audiovox) programmed for a 5 second vacuum and a 3.9 second seal time.

Packaged LSE units were placed into the programmable freezer (Planar) at a starting temperature of 20.0° C. LSE units were cooled at −10.0° C./minute to −6.0° C. and the chamber temperature was held at −6.0° C. for 20 minutes to equilibrate the constructs to the chamber temperature. After the 20 minute hold, extracellular ice was initiated by contact of the outside of the bag, below the level of the freeze media, with a liquid nitrogen chilled probe. After all LSE units were seeded with ice crystals, the chamber temperature was held for an additional 5 minutes at −6.0° C. The chamber temperature was then cooled at −1.0° C./minute to −8.0° C. The chamber temperature was held again for 30 minutes at −8.0° C. to allow for uniform distribution of ice throughout the sample. The freezer temperature was then cooled at −0.1° C./minute to a final temperature of −70.0° C.

Cryopreserved LSE were removed from the freezer and the bag was cut from the petri dish. The lid of the dish was removed and 40 mL of warmed (37° C.) DMEM was aseptically poured into the petri dish. After 45 seconds, all liquid was removed from the dish and an additional 40 mL aliquot was added to the dish for two minutes. Once thawed, the LSE unit and attached transwell were transferred to a new petri dish, using sterile forceps. To rinse the LSE of cryoprotectant, 25 mL of DMEM was added to the petri dish containing the LSE for 30 minutes. The media was exchanged a second time for an additional 30 minutes. The LSE unit was then transferred back to its original culture dish and was incubated in culture maintenance medium at 37° C./10% $CO_2$ for 24 hours prior to analysis. The incubation time was allowed for the lag typically seen for frozen cells to reestablish steady state conditions.

Figure 1B:
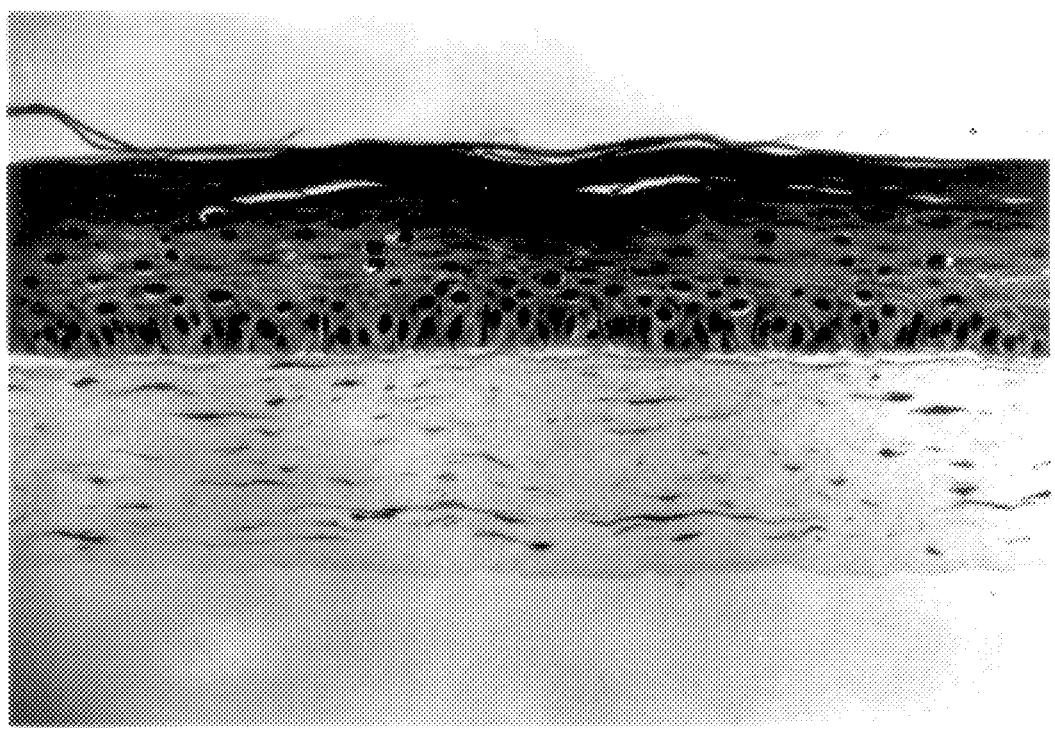

Thawed cryopreserved and control samples were evaluated and analyzed using histology (FIG. 1), MTT assay, LDH assay, and graft study.

Example 2

Cryopreservation of Epidermal Sheets

Epidermal sheets were procured from mature LSE at 12 days post air-lift. Removal of the epidermal sheet was accomplished by peeling the dermal substrate layer from the epidermal layer with forceps and discarding the dermal layer. Each sheet was cut in to three equivalent pieces. One piece from each sheet was fixed as a control. The remaining two pieces form each sheet were placed on top of a 75 mm polycarbonate transwell membrane (Costar) in 100 mm culture dishes (Costar). Each piece was perfused with 25 mL of DMEM and 2 Molar Glycerol for one hour. The dishes containing constructs were placed on an orbital shaker (Bellco) at 70 rpm for one hour in a 10% $CO_2$ gassed chamber. After the epidermal sheet was perfused, the petri dish containing epidermal sheet, transwell and extracellular freezing media (2M Glycerol and DMEM) were placed in a bag and vacuum sealed (Audiovox) programmed for a 5 second vacuum and a 3.9 second seal time.

Packaged epidermal sheets were placed into the programmable freezer (Planer) at a starting temperature of 20.0° C. Epidermal sheets were cooled at −10.0° C./minute to −6.0° C. The temperature was allowed to hold for 20 minutes at −6.0° C. to equilibrate to chamber temperature. After the 20 minutes hold, extracellular ice was initiated by contact of the outside of the bag, below the level of the freeze media, with a liquid nitrogen chilled probe. After all epidermal sheets had been seeded with ice crystals, the temperature was held an additional 5 minutes at −6.0° C. The chamber was then cooled at −1.0° C./minute to −8.0° C. The temperature was then allowed to hold for 30 minutes at −8.0° C. to allow for uniform distribution of ice throughout the sample. The chamber was then cooled at −0.1° C./minute to a final temperature of −70.0° C.

Cryopreserved epidermal sheets were removed from the freezer and the bags were cut from the petri dishes and the lids removed. To thaw, 40 mL of warmed (37° C.) DMEM was aseptically poured into each petri dish. After 45 seconds, all liquid was removed from the dishes and an additional 40 mL aliquot was added to each dish for two minutes After all ice was thawed, epidermal sheets were rinsed with 25 mL of DMEM for 30 minutes. The media was exchanged a second time for an additional 30 minutes. The epidermal sheets were then incubated in culture maintenance medium at 37° C./10% CO2 for 24 hours prior to analysis. The incubation time was allowed for the lag typically seen for frozen cells to reestablish steady state conditions. Again, the incubation time was allowed for the lag typically seen for frozen cells to reestablish steady state conditions.

Figure 2A:
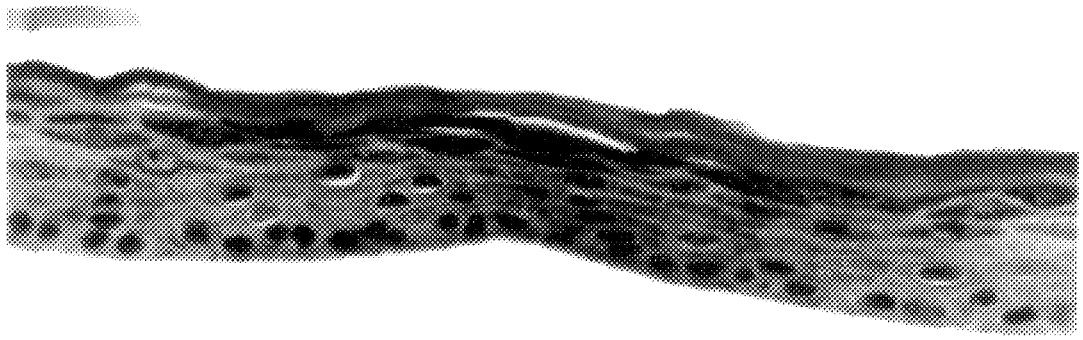
FIGS. 2A–2B show photomicrographs of non-cryopreserved epidermal sheet (2A) and cryopreserved epidermal sheet (2B) of Example 2. The three basic features of the epidermis: the basal layer of the epidermis, the suprabasal layers of the epidermis and the stratum corneum of the epidermis are all preserved by this method. All layers are intact and the overall morphology of the cryopreserved epidermal sheet is identical to that of the non-cryopreserved epidermal sheet.
Figure 2B:
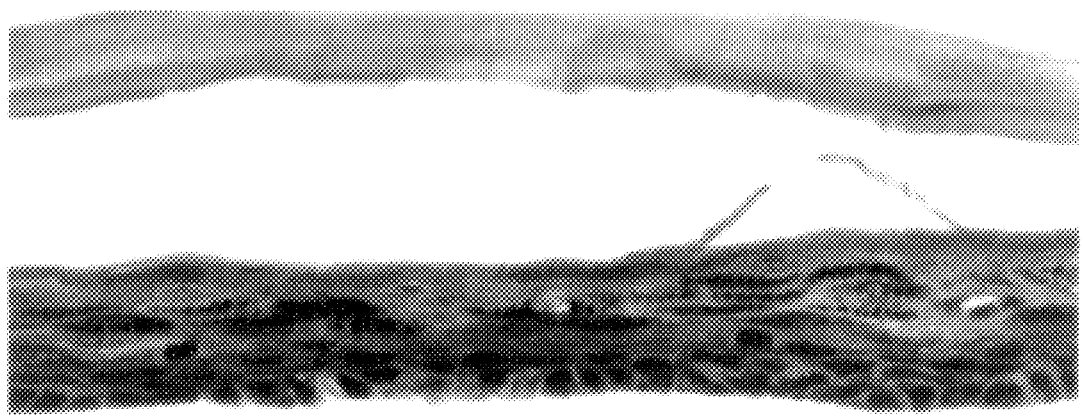

Of the two remaining pieces from each epidermal sheet, one from each was processed for histology (FIG. 2) and one piece from each sheet was assayed following the MTT assay protocol.

Example 3

Cryopreservation of Dermal Equivalent

Dermal equivalents used in this study were the non-epidermalized component of the LSE. Dermal equivalents were frozen at 8 days post cast. The dermal equivalents were perfused with cryoprotectant by submerging the dermal equivalents attached to 75 mm transwell (Costar) placed in 100 mm petri dishes (Costar) with 25 mL of DMEM and 2 Molar Glycerol for one hour. The petri dishes were placed on an orbital shaker (Bellco) at 70 rpm for one hour in a 10% CO2 gassed chamber. After dermal equivalents were perfused, the petri dishes, dermal equivalents, transwells and extracellular freezing media were placed into the programmable freezer (Planer) at a starting temperature of 20.0° C. The chamber was then cooled at −10.0° C./minute to −6.0° C. The temperature was held for 20 minutes to equilibrate to chamber temperature. After the 20 minutes hold, extracellular ice was initiated by contact of the outside of the dishes, below the level of the freeze media, with a liquid nitrogen chilled probe. After all dermal equivalents had been seeded with ice crystals, the temperature was held an additional 5 minutes at −6.0° C. The chamber was then cooled at −1.0° C./minute to −8.0° C. The chamber temperature was held again for 30 minutes at −8.0° C. to allow for uniform distribution of ice throughout the sample. Dermal equivalents units were then cooled at −0.1° C./min. to a final temperature of −70.0° C.

Cryopreserved dermal equivalents were then removed from the freezer and the lid of the dish was removed. To thaw, 40 mL of warmed (37° C.) DMEM was aseptically poured into each petri dish. After 45 seconds, all liquid was removed from the dishes and an additional 40 mL aliquot was added to the dishes for two minutes After all ice was thawed, dermal equivalents were rinsed with 25 mL of DMEM for 30 minutes The media was exchanged a second time for an additional 30 minutes The dermal equivalents, still attached to the transwells, were then transferred back to the culture dishes and incubated in culture maintenance medium at 37° C./10% $CO_2$ for 24 hours prior to analysis. The incubation time was allowed for the lag typically seen for frozen cells to reestablish steady state conditions. Samples were assayed using the MTT assay protocol.

Example 4

Cryopreservation of Cornea Equivalents

Cornea equivalents, attached to 24 mm culture transwells (Costar), 9 days post moist air lift, were placed into six well cluster dishes (Costar). The method of perfusing cornea equivalents with cryoprotectant was to submerge each cornea equivalent and transwell with 4 mL extracellular freezing media (2M glycerol in DMEM) in the six well cluster dishes for one hour. The six well cluster dishes containing the cornea constructs were shaken for one hour on an orbital shaker (Bellco) at 70 rpm in a 10% $CO_2$ gassed chamber. After cornea equivalents were perfused, the petri dishes containing cornea equivalents, transwells and extracellular freezing media were placed into the programmable freezer (Planer) at a starting temperature of 20.0° C. Cornea equivalents were cooled at −10.0° C./min. to −6.0° C. The temperature was held for 20 minutes to equilibrate to chamber temperature. After the 20 minutes hold, extracellular ice was initiated by contact of the outside of each well in the cluster plate, below the level of the freeze media, with a liquid nitrogen chilled probe. After all cornea equivalents had been seeded with ice crystals the temperature was held an additional 5 minutes at −6.0° C. prior to cooling at −1.0° C./minute to −8.0° C. The temperature was held again for 30 minutes at −8.0° C. to allow for uniform distribution of ice throughout the sample. Cornea equivalent units were cooled at −0.1° C./minute to a final temperature of −70.0° C.

Cryopreserved cornea equivalents were removed from the freezer. The lid of the dish was removed. To thaw, 6 mL of warmed (37° C.) DMEM was aseptically poured into each well of the cluster plate. After 45 seconds, all liquid was removed from the dish and an additional 6 mL aliquot was added to the dish for two minutes Using sterile forceps the cornea equivalents and attached transwells was transferred to a new cluster dish. To rinse, 4 mL of DMEM was added to each well for 30 minutes. The media was exchanged a second time for an additional 30 minutes The cornea units were then transferred back to the/same culture dish and incubated in cornea maintenance medium at 37° C./10% $CO_2$ for 24 hours prior to analysis. The incubation time was allowed for the lag typically seen for frozen cells to reestablish steady state conditions. Samples were assayed using the MTT assay protocol.

Example 5

Cryopreservation of Harvested Murine Skin

Wild type mice, strain B6CB6YF1, were euthanized by Nembutal overdose. The skin was harvested aseptically. Excess blood vessels, fat and connective tissue were removed from the dermis. Murine skin was trimmed to a rectangular 1 cm×2 cm piece. Murine skin pieces were then placed on a 75 mm transwell (Costar) in 100 mm petri dishes (Costar). Murine skin was perfused with cryoprotectant by submerging in 25 mL of 2M Glycerol in DMEM in the 100 mm petri dishes for one hour. During perfusion, the petri dishes each containing the murine skin and the transwell were shaken for one hour on an orbital shaker (Bellco) at 70 rpm in a 10% CO2 gassed chamber. Control, non-cryopreserved mouse skin was kept in nutrient media at 4° C. for the duration of the cryopreservation and thawing process (2 days) before skin grafting.

After murine skin is perfused, the petri dishes containing murine skin, transwells and extracellular freezing media are placed into the Planer programmable freezer at a starting temperature of 20.0° C. Murine skin was cooled at −10.0° C./minute to −6.0° C. and were allowed to hold at −6.0° C. for 20 minutes to equilibrate to chamber temperature. After the 20 minute hold, extracellular ice was initiated by contact of the outside of the dish with a liquid nitrogen chilled probe. The contact site must be below the level of the freeze media. After all murine skin had been seeded with ice crystals, the temperature was held an additional 5 minutes at −6.0° C. prior to cooling at −1.0° C./minute to −8.0° C. The temperature was held again for 30 minutes at −8.0° C. to allow for uniform distribution of ice throughout the sample. The units were then cooled at −0.1° C./min. to a final temperature of −70.0° C.

Cryopreserved murine skin was removed from the freezer and the lid of the dish was removed. To thaw, 40 mL of warmed (37° C.) DMEM was aseptically poured into the petri dishes. After 45 seconds, all liquid was removed from the dishes and an additional 40 mL aliquot was added to the dishes for two minutes After all ice was thawed, murine skin was rinsed in the dishes with 25 mL DMEM for 30 minutes The media was exchanged a second time for an additional 30 minutes.

Figure 3A:
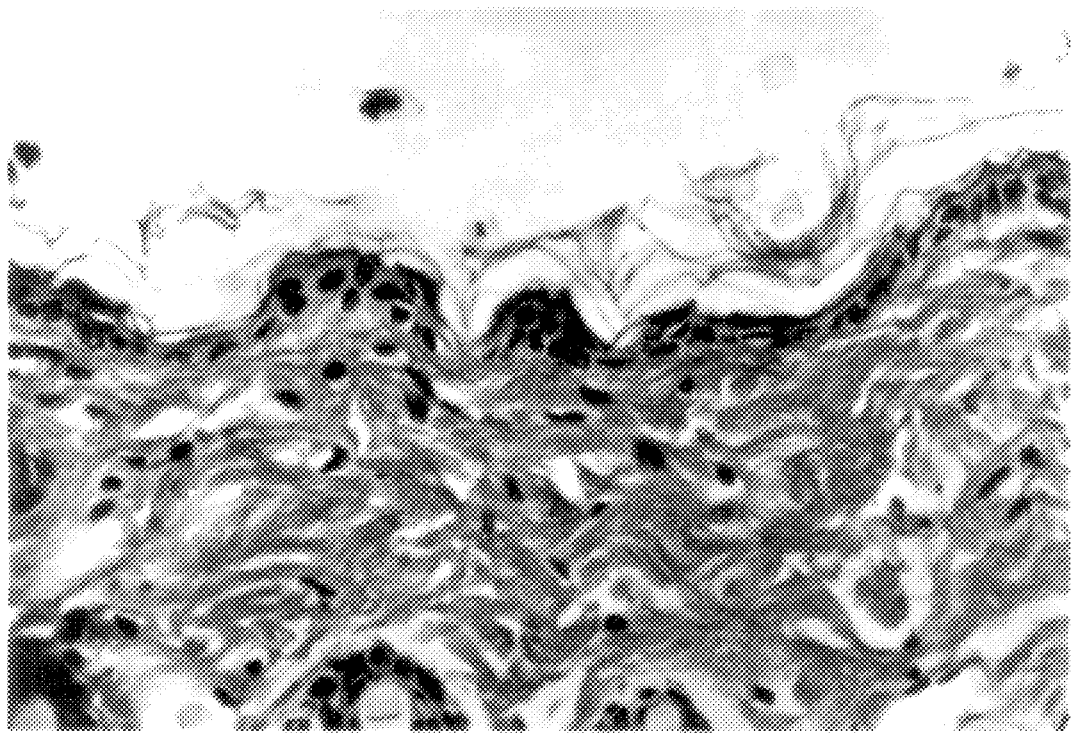
FIGS. 3A–3B show photomicrographs of non-cryopreserved mouse skin (3A) and cryopreserved mouse skin (3B) of Example 5. The four basic features of mouse skin, the dermis with fibroblasts, the basal layer of the epidermis, the suprabasal layers of the epidermis and the stratum corneum of the epidermis are preserved by this method. All layers are intact and the overall morphology of cryopreserved mouse skin is identical to that of non-cryopreserved mouse skin.
Figure 3B:
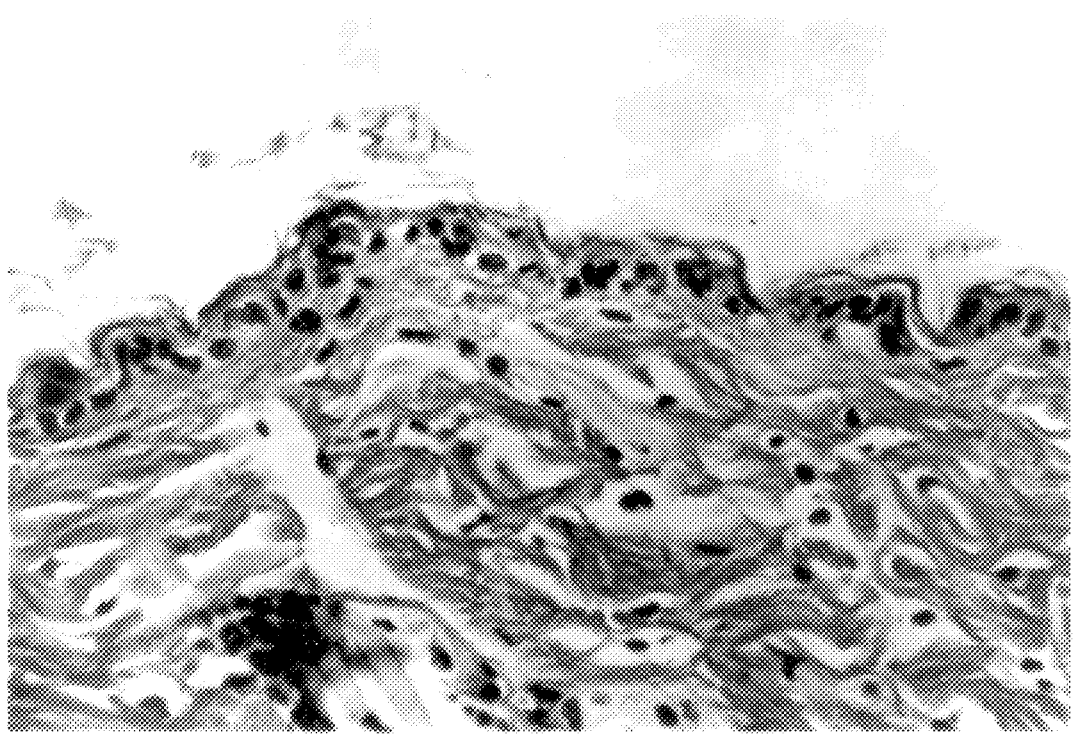

Thawed cryopreserved and control samples were processed for histology (FIG. 3) or were grafted to mice.

Example 6

Cryopreservation of ATS SKIN2™

SKIN2™, model ZK1300 (Advanced Tissue Sciences, La Jolla, Calif.), was removed from the packaging according to shipping inserts upon arrival and were placed in culture dishes (Costar). Transwell inserts were placed above the SKIN2™ to keep the skin construct submerged. SKIN2™ was perfused with cryoprotectant by submerging SKIN2™ in 2M Glycerol in DMEM in the culture dishes for one hour. During perfusion, the culture dishes containing the construct and the transwell were shaken for one hour on an orbital shaker (Bellco) at 70 rpm in a 10% $CO_2$ gassed chamber.

After SKIN2™ is perfused, the units were placed into the programmable freezer (Planar) at a starting temperature of 20.0° C. SKIN2™ units were cooled at −10.0° C./min. to −6.0° C. and were allowed to hold at −6.0° C. for 20 minutes to equilibrate to the chamber temperature. After the 20 minute hold, extracellular ice was initiated by contact of the outside of the dishes below the level of the freeze media with a liquid nitrogen chilled probe. After all SKIN2™ units were seeded with ice crystals, the temperature was held for an additional 5 minutes at −6.0° C. The chamber temperature was then cooled at −1.0° C./min. to −8.0° C. SKIN2™ units were allowed to hold for 30 minutes at −8.0° C. to allow for uniform distribution of ice throughout the sample. SKIN2™ units were then cooled at −0.1° C./min. to a final temperature of −70.0° C.

Cryopreserved SKIN2™ were removed from the freezer, the lids of the dishes was removed and warmed (37° C.) DMEM was aseptically poured into each culture dish. After 45 seconds, all liquid was removed from the dishes and another addition of DMEM was added to each dish for two minutes. Once thawed, the SKIN2™ unit and attached transwell were transferred to a new culture dishes, using sterile forceps. To rinse the SKIN2™ of cryoprotectant, DMEM was added to each culture dish containing the SKIN2™ for 30 minutes. The media was exchanged a second time for an additional 30 minutes. The SKIN2™ unit was then transferred back to the same type culture dish and was incubated in culture maintenance medium at 37° C./10% CO2 for 24 hours prior to analysis. Again, the incubation time was allowed for the lag typically seen for frozen cells to reestablish steady state conditions.

Figure 4A:
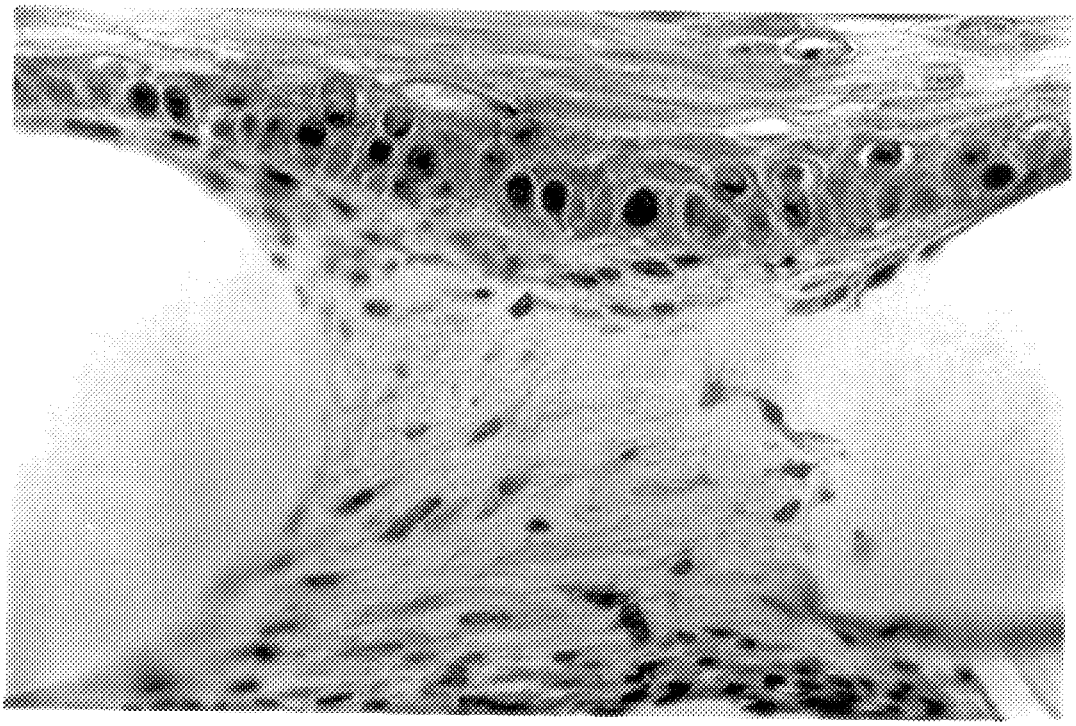
FIGS. 4A–4B show photomicrographs of non-cryopreserved SKIN2™ (4A) and cryopreserved SKIN2™ (4B) of Example 6. The four basic features of SKIN2™, the collagen lattice with fibroblasts, the basal layer of the epidermis, the suprabasal layers of the epidermis and the stratum corneum of the epidermis are preserved by this method. All layers are intact and the overall morphology of cryopreserved SKIN2™ is similar to that of non-cryopreserved SKIN2™.
Figure 4B:
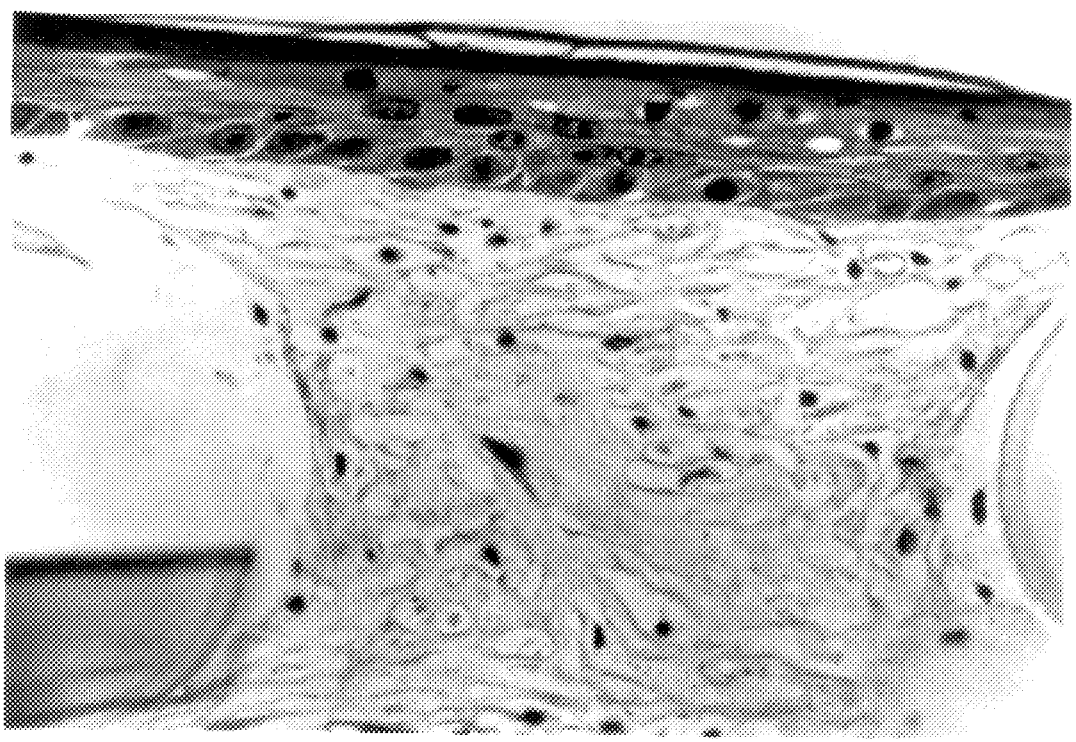

Cryopreserved and control constructs were assayed following the MTT assay protocol for SKIN2™ model ZK1300, enclosed with the product, and also by histological evaluation (FIG. 4).

Example 7

Metabolic Mitochondrial Activity Assay (MTT)

Frozen and non-frozen (control) LSE, epidermal sheet, dermal equivalents and corneal equivalents were tested using the MTT assay. [SKIN2™ constructs were assayed according to "MTT Assay Protocol for use with Model ZK1300", enclosed with the shipping inserts.] Cell viability of the constructs were measured using the MTT assay, a calorimetric MTT conversion assay developed to measure cellular growth and viability. This assay is described in detail in Gay et al., "The Living Skin Equivalent as a Model In Vitro for Ranking the Toxic Potential of Dermal Irritants," Toxic. in Vitro, 6:303–315 (1992). The metabolic reduction of the soluble tetrazolium salt to a blue formazan precipitate is dependent on the presence of viable cells with intact mitochondrial function. This assay is used to quantitate cytotoxicity in a variety of cell types, including cultured human keratinocytes.

Figure 5:
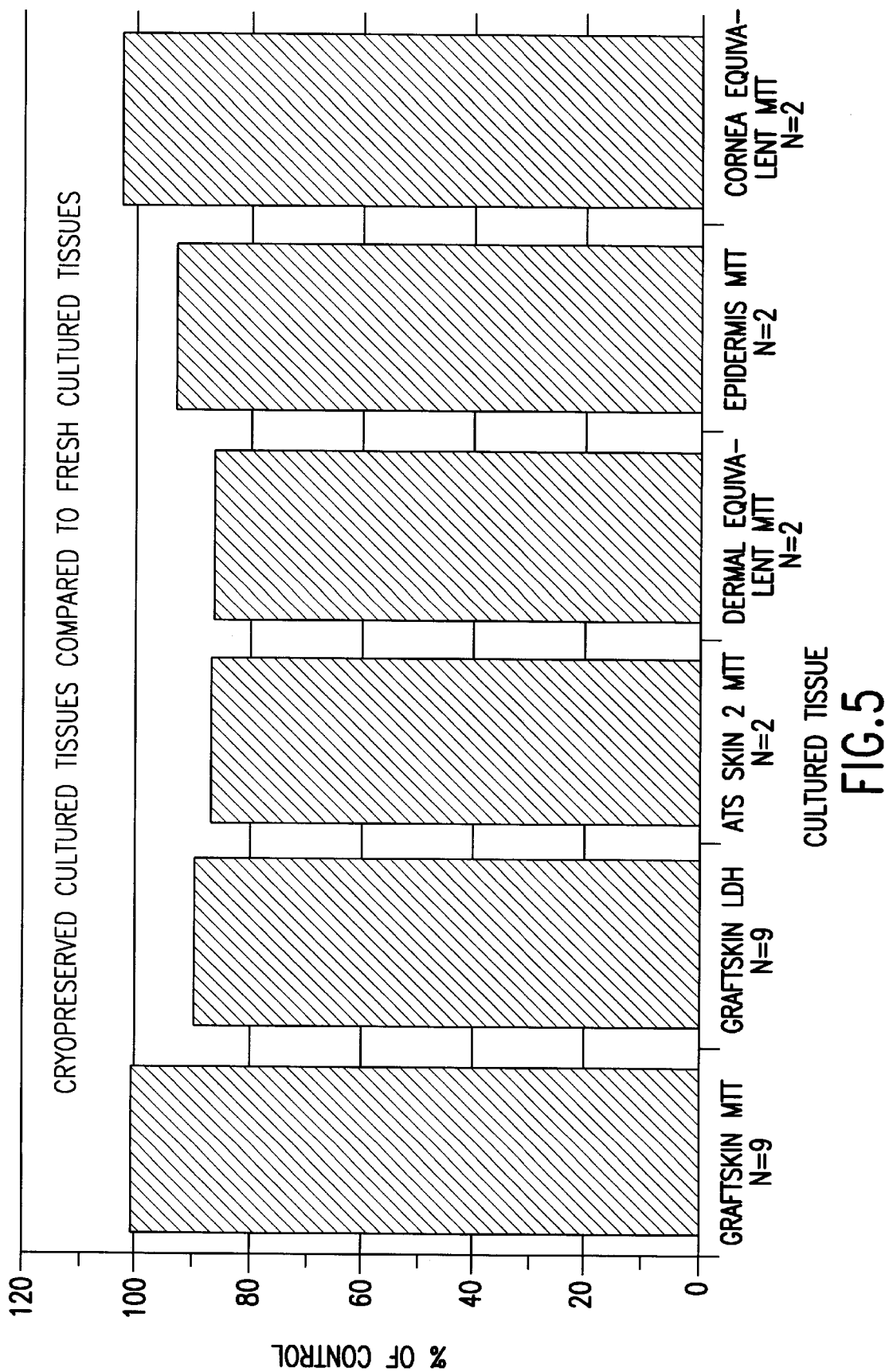
FIG. 5 shows a graph of the viability of cryopreserved cultured tissues compared that of non-cryopreserved cultured tissues. The viability of cryopreserved cultured tissues as measured by MTT is shown. LSE was additionally measured by LDH assay. All cultured tissues are compared to age-matched non-cryopreserved controls and are expressed as a percent of control.

To the culture dishes containing LSE, epidermal sheet and dermal equivalent, 40 mL of assay medium and to the wells containing corneal equivalents, 1.5 mL of assay medium containing 0.33 mg/mL MTT (Sigma Chemical Co., St. Louis, Mo.) was added. The tissue equivalents were incubated in the MTT assay medium for 3–4 hours. At the end of the conversion period, the tissue equivalent was biopsied using an 8-mm diameter skin biopsy punch. The punch biopsies were then extracted for 2–3 hours at room temperature in 0.3 mL isopropanol, acidified with 0.04N HCl. At the end of the extraction period, 0.2 mL of each extract was transferred to a well of a 96-well plate. The absorbencies were read on a plate reader (Dynatech) at 570 nm with the isopropanol extraction medium as a blank. MTT values obtained from thawed cryopreserved samples were compared to corresponding control samples and expressed in terms of percent of control (FIG. 5).

Example 8

Lactose Dehydrogenase Assay (LDH)

LDH is an enzyme typically found in a viable cell. Damage to the cell causes a release of the enzyme and a corresponding decrease in the enzyme activity detected by this assay.

Thawed cryopreserved and control samples of LSE were punched with an 8 mm diameter skin biopsy punch. Three samples were taken from each LSE unit. Punch samples were placed in a 15 mm tubes with 1 mL of 0.1M triethanolamine buffer (on ice) and homogenized with an electric tissue homogenizer for one minute. The samples were then centrifuged at 1000 g at 4.0° C. The supernatant was then assayed. LDH cocktail reagent was prepared by mixing together the following: 3.00 mL phosphate buffer (0.1 mol/l; pH 7.0), 0.1 mL pyruvate, Na salt (2.5 mg/mL), and 0.05 mL NADH, Na salt (10 mg/mL). 100 $\mu$L of sample supernatant was added to 900 $\mu$L of the reagents and allowed to react for two minutes. The change in absorbance over the two minutes was recorded. The average of three samples per cryopreserved LSE unit were compared to the non-frozen controls. Sample values were compared to corresponding control values and expressed in terms of percent of control (FIG. 5).

Example 9

Bioequivalence of Cryopreserved LSE to non-Cryopreserved LSE

To demonstrate the bioequivalence of cryopreserved and non-cryopreserved LSE, a grafting study to athymic mice was performed.

LSE units, cryopreserved according to the method outlined in Example 1, were thawed one day before grafting and recovered in maintenance media for twenty-four hours.

Four experiments were performed in which a total of 66 athymic mice of the strain B6CB6YF1/J-nu (Jackson Harbor Labs) were grafted with either cryopreserved LSE (n=43) or non-cryopreserved (control) LSE (n=23). Animals were anesthetized with Nembutal. A 2×2 cm full thickness skin section was excised from the dorsum of each mouse, sparing the panicculus carnosus. LSE grafts, either control or cryopreserved, were placed on the wound and trimmed to fit. All grafts were dressed with one layer of petrolatum impregnated gauze (vendor) and covered by two adhesive bandages (vendor). The dressings were removed at 7 days post-graft.

Figure 6A:
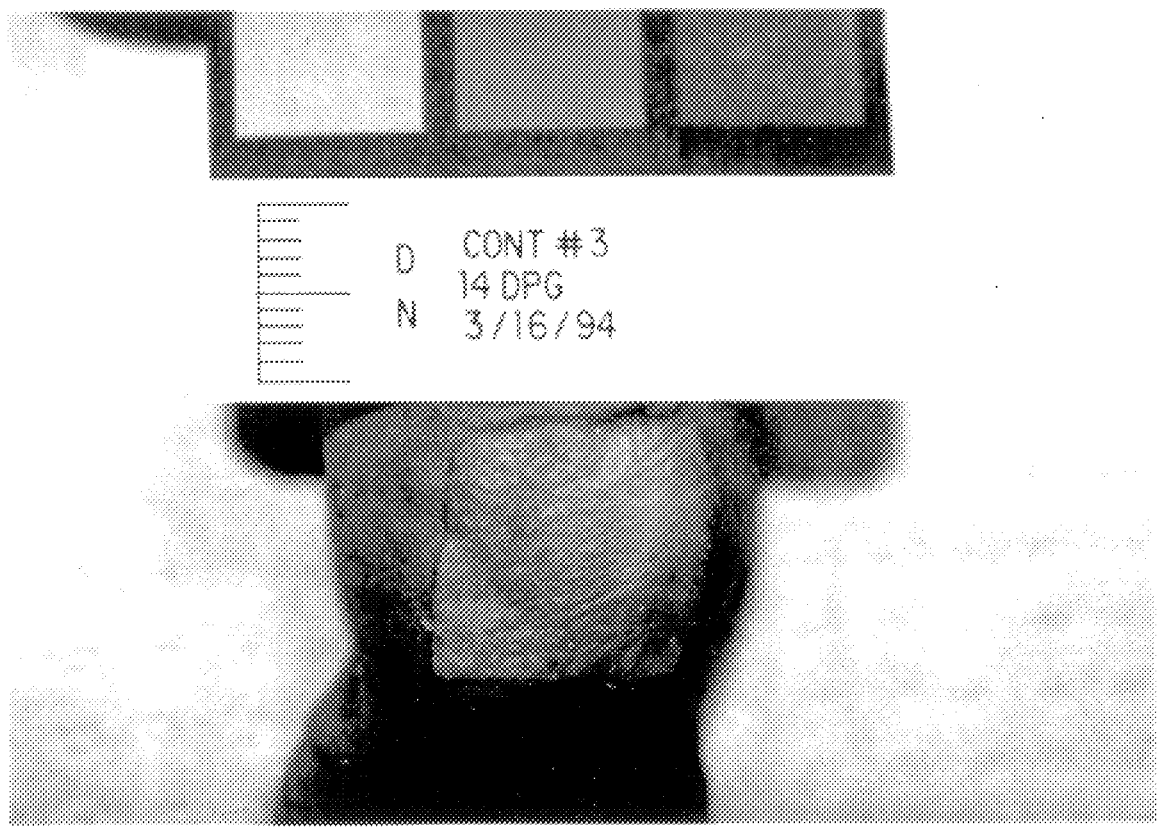
FIGS. 6A to 6D show comparative results.
Figure 6B:
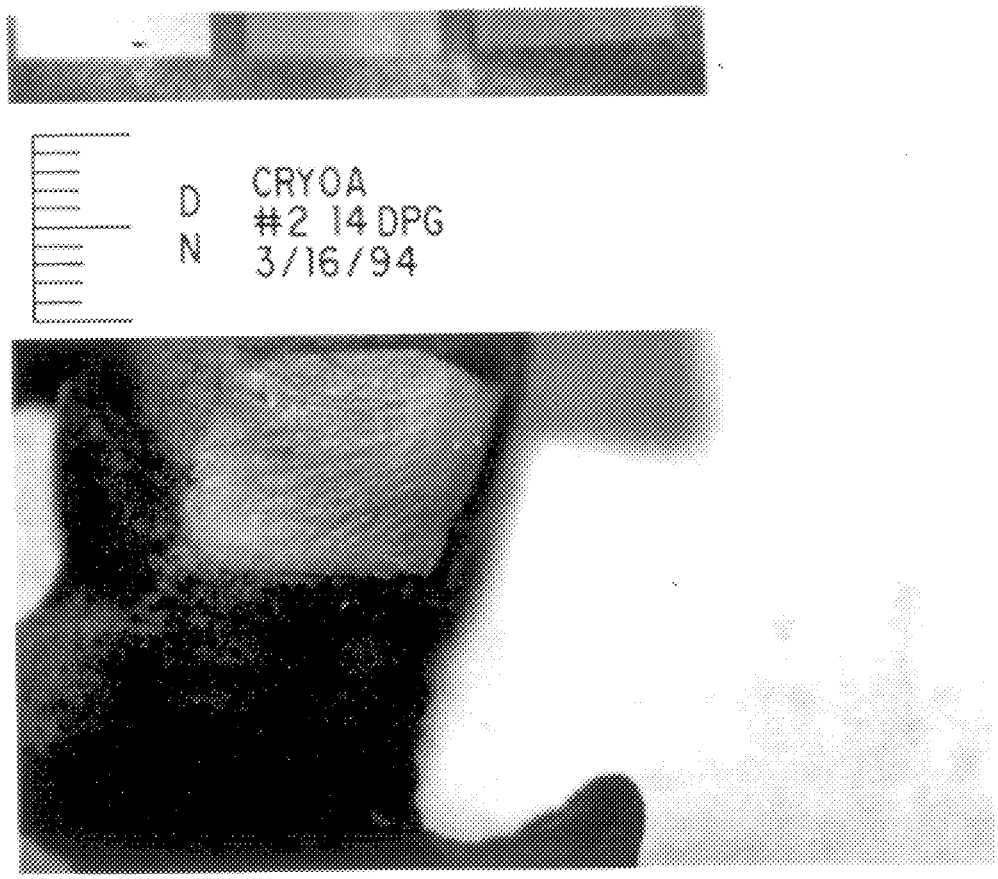
Figure 6C:
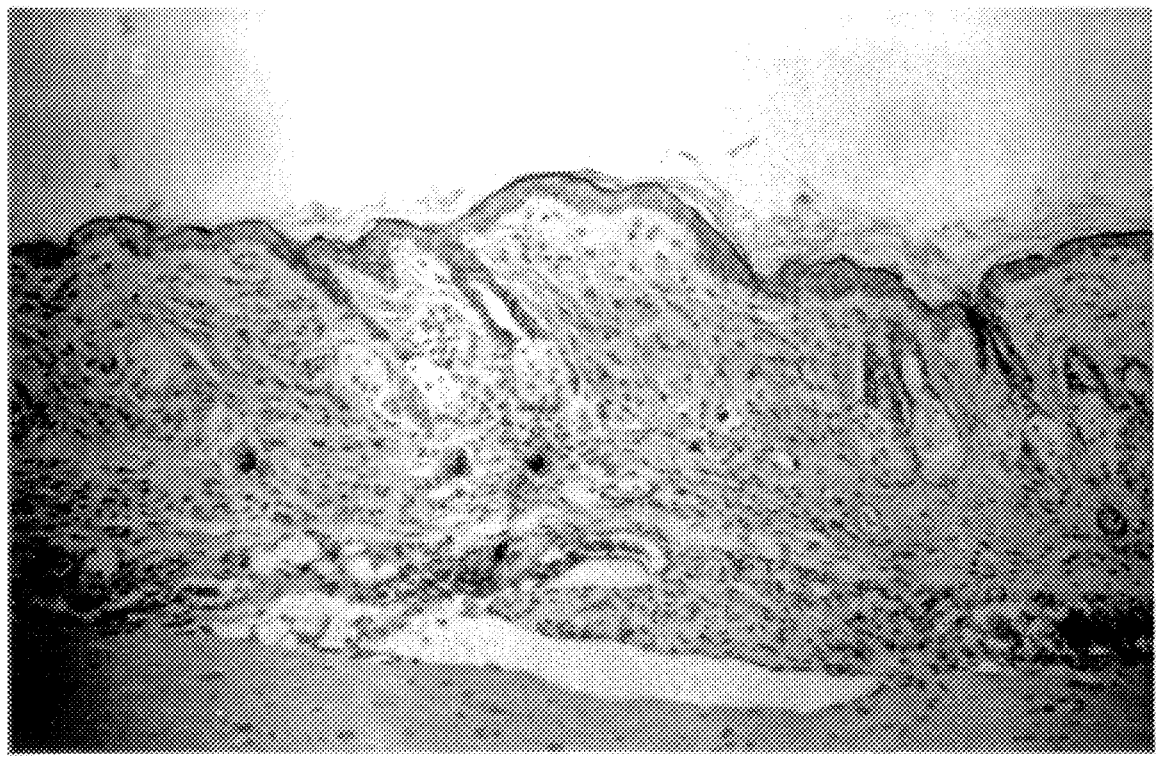
Figure 6D:
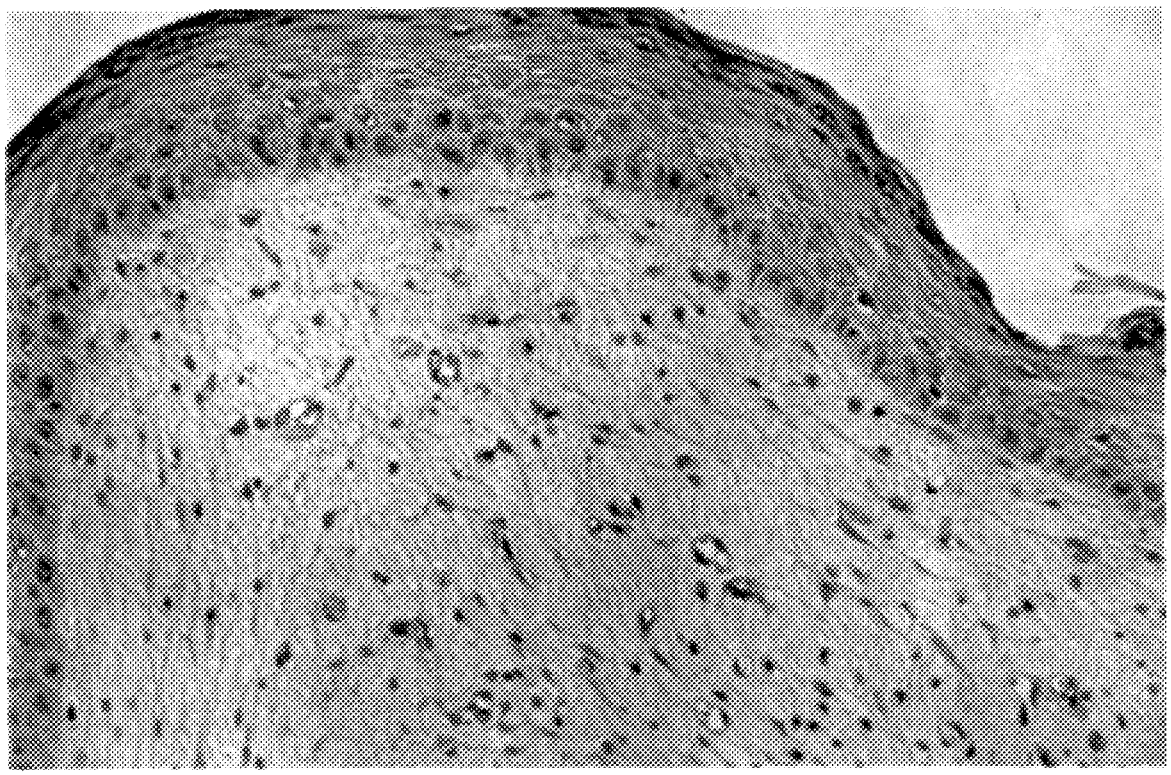

At 14 days post-graft, all animals were euthanized and photographed. The graft site was then excised for histological analysis and evaluation. The gross photographs (FIGS. 6A, B) and micrographs (FIGS. 6C, D) show no difference in graft integration between control LSE or thawed, cryopreserved LSE. No significant difference was seen in rates of wound contracture between control or cryopreserved grafts.

Example 10

Syngenaic Skin Grafting of Cryopreserved and Control Mouse Skin

To demonstrate the bioequivalence of cryopreserved and non-cryopreserved mouse skin, a syngenaic skin grafting study was performed.

Wild type mice, strain B6CB6YF1, were euthanized by Nembutal overdose. The skin was harvested aseptically. Excess blood vessels, fat and connective tissue were removed from the dermis in preparation for skin grafting. Mouse skin was cryopreserved and thawed following the method in Example 5. Control, non-cryopreserved mouse skin was kept in a nutrient media at 4° C. for the duration of the cryopreservation and thawing process, a total of two days, before skin grafting.

Six mice of the same strain received skin grafts, two received control, non-cryopreserved mouse skin and four received thawed, cryopreserved mouse skin. The mice were anesthetized with Nembutal. A 2×2 cm full thickness skin section was excised from the dorsum of each mouse, sparing the panicculus carnosus. Mouse skin grafts, either control or cryopreserved, were placed on the wounds and trimmed to fit. All grafts were dressed with one layer of petrolatum impregnated gauze, covered by two adhesive bandages. These dressings were removed at 7 days post-graft.

Figure 7A:
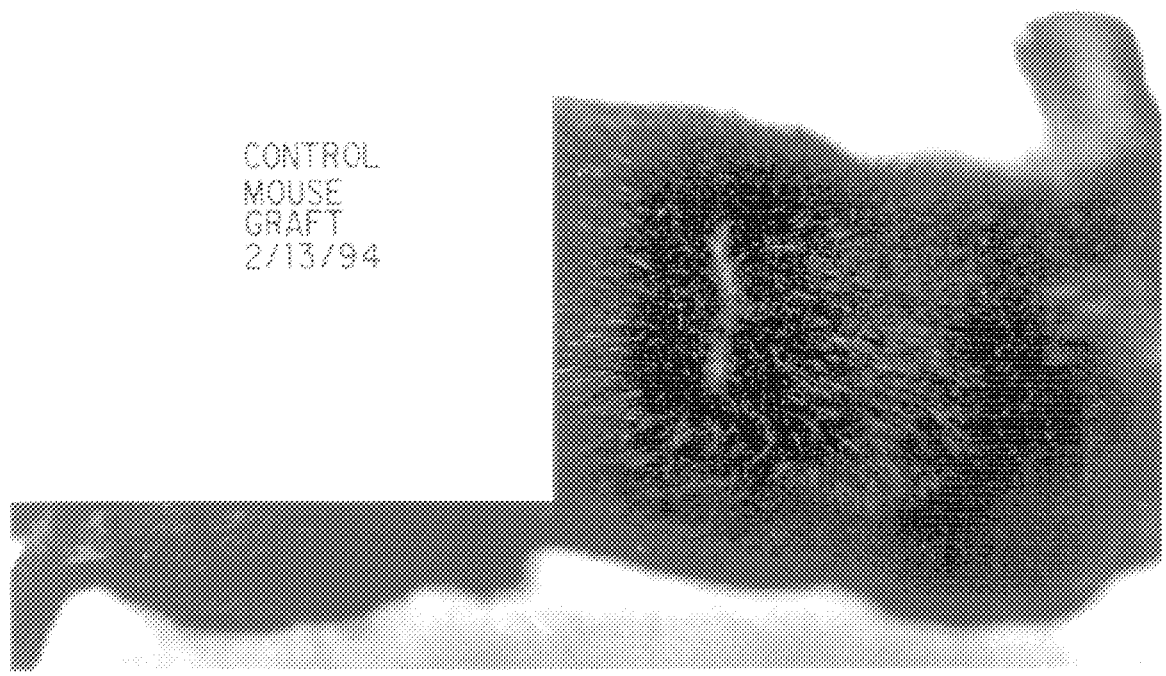
FIGS. 7A to 7D show comparative results.
Figure 7B:
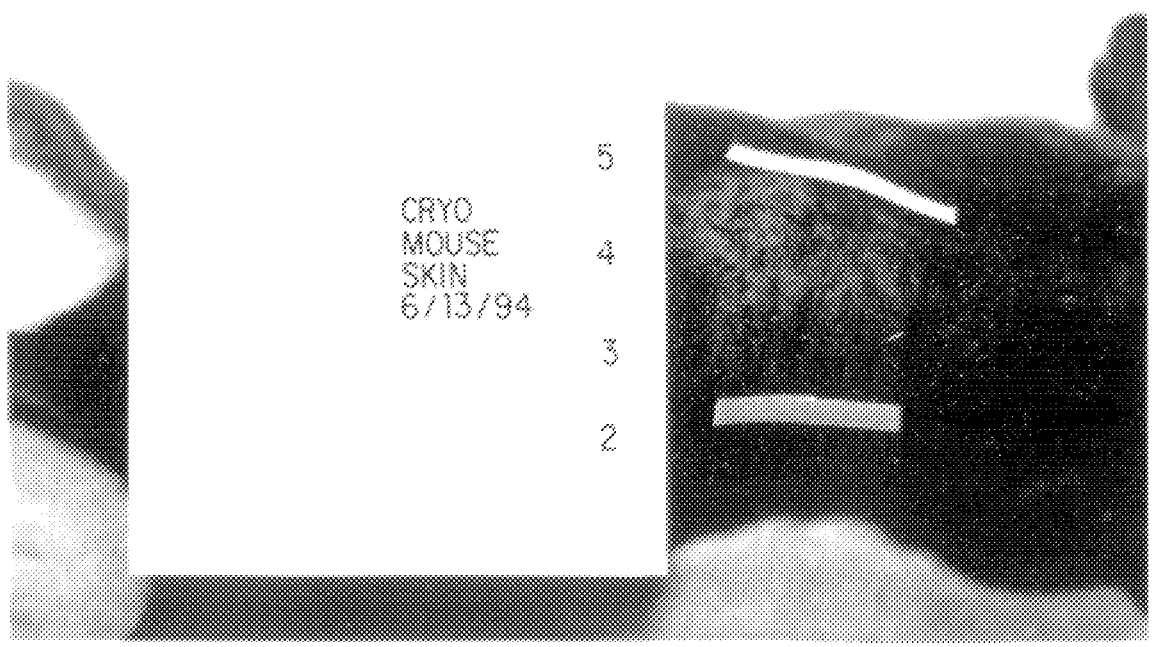
Figure 7C:
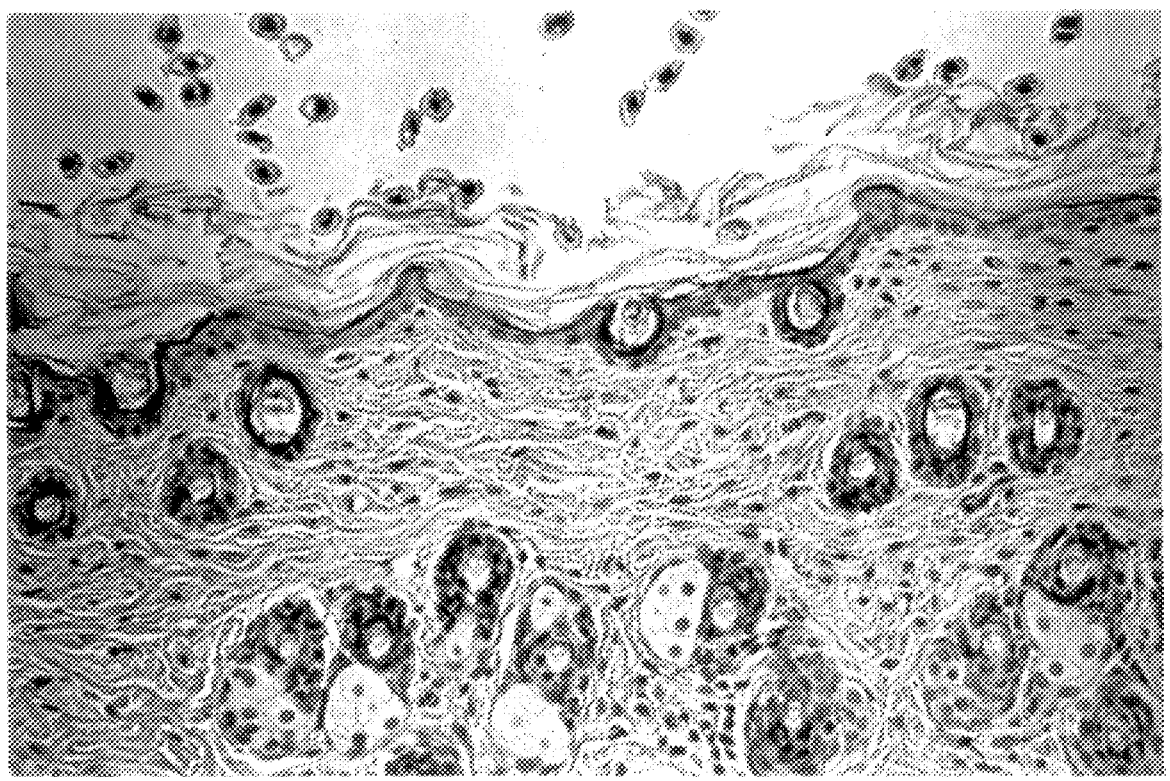
Figure 7D:
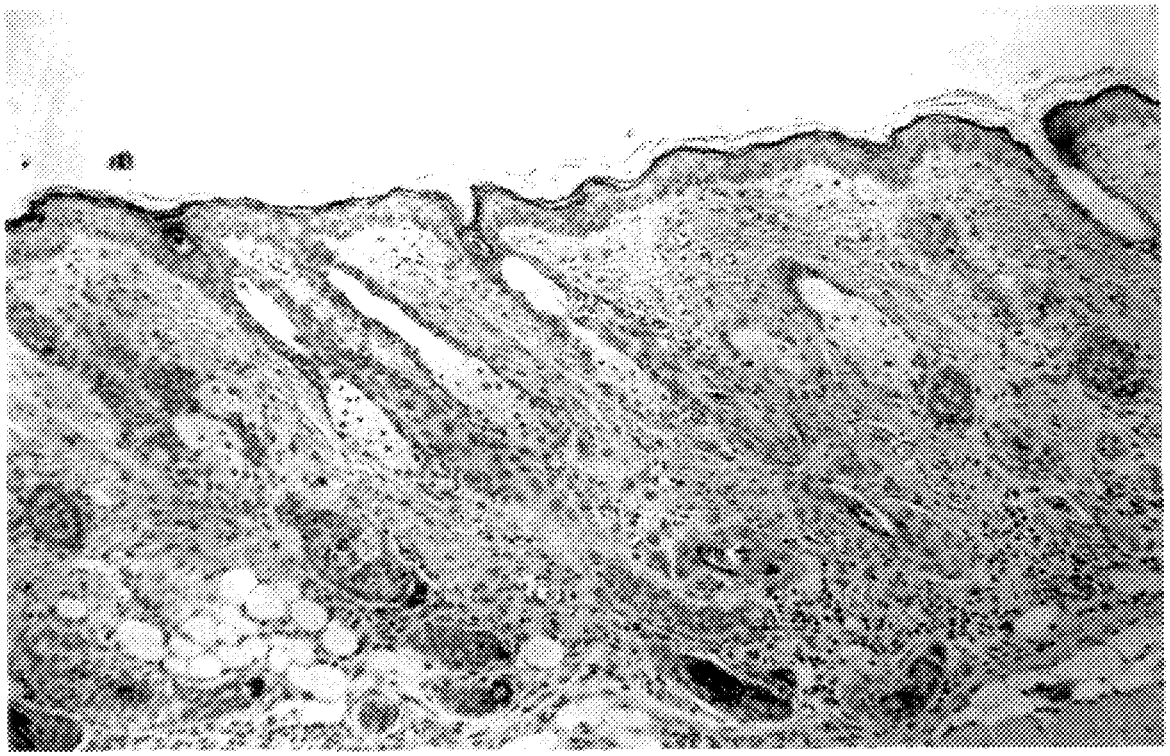

At thirty days post-graft, all animals were euthanized and photographed. The graft site was then excised for histological analysis and evaluation. The gross photographs (FIGS. 7A, B) and micrographs (FIGS. 7C, D) show that there is no difference in graft integration between control mouse skin or thawed, cryopreserved mouse skin. No significant difference was seen in rates of wound contracture between control or cryopreserved grafts.

Although the foregoing invention has been described in some detail by way of illustration and example for purposes of clarity of understanding, it will be obvious to one skilled in the art that certain changes and modifications may be practiced within the scope of the appended claims.

What is claimed is:

1. A method for cryopreserving a harvested mammalian skin or cultured skin or cornea equivalent, comprising:

(a) immersing said tissue in a cryoprotectant solution and agitating said cryoprotectant solution and said immersed tissue to achieve effective penetration of the cryoprotectant solution into said tissue;

(b) lowering the temperature sufficient to permit ice seeding and seeding extracellular ice in said cryoprotectant solution; and (c) cooling to a cryopreserved state said cryoprotectant solution and said tissue at a rate of about −0.3° C. per minute or less to a temperature sufficient to cryopreserve said tissue.

2. The method of claim 1 wherein said immersion in step (a) is accomplished in a gassed environment.

3. The method of claim 1 wherein in step (b) extracellular ice is initiated by contact with a liquid nitrogen chilled probe.

4. The method of claim 1 wherein after said ice seeding the temperature is lowered at a rate of −1° C./minute to a temperature of about −8° C. and held for a time sufficient to allow for physical and biological equilibration of said cryoprotectant solution in said tissue, prior to cooling to a cryopreserved state.

5. The method of claim 4 wherein said cooling rate in step (c) is about −0.2° C. per minute or less.

6. The method of claim 4 wherein said cooling rate in step (c) is about −0.1° C. per minute or less.

7. The method of claim 1 wherein said cultured skin equivalent is selected from the group consisting of cultured epidermal equivalent, cultured dermal equivalent, bilayered skin equivalent and trilayered skin equivalent.

8. The method of claim 1 wherein said temperature of said cryopreserved state is at or below −120° C.

9. The method of claim 1 wherein said temperature of said cryopreserved state is at or below −140° C.

10. The method of claim 1 wherein said temperature of said cryopreserved state is at or below −196° C.

11. The method of claim 1 wherein said cryoprotectant solution is 1.5M to 2.5M glycerol in a medium of Dulbecco's Modified Eagle's Medium.

12. The method of claim 1 further comprising thawing said cryopreserved tissue, wherein said tissue is thawed in about 1 to about 3 minutes.

13. The method of claim 1 wherein said cryoprotectant solution comprises one or more glass-forming agents selected from the group consisting of a cell penetrating, glass-forming agent and a non cell-penetrating glass-forming agent.

14. The method of claim 13 wherein said non cell-penetrating, glass-forming agent is a high molecular weight form of a complex carbohydrate comprising one or more members selected from the group consisting of chondroitin sulfate, polyvinylpyrrolidone, and polyethylene glycol.

15. The method of claim 13 wherein said non cell-penetrating, glass-forming agent is a hetastarch.

16. The method of claim 15 wherein said hetastarch is hydroxyethyl starch.

17. The method of claim 13 wherein said cell-penetrating, glass-forming agent is selected from the group consisting of: glycerol, propylene glycol, ethylene glycol, and dimethyl sulfoxide.

18. The method of claim 17 wherein said cell penetrating agent is glycerol.

19. The method of claim 13 wherein said glass-forming agent is diluted in a medium selected from the group consisting of DMEM, IDMEM, MEM, M199, RPMI 1640, Ham's F-12, Ham's F-10, NCTC 109, NCTC 135, and phosphate buffered saline.

20. The method of claim 1 wherein said cryoprotectant solution is 2M glycerol in Dulbecco's Modified Eagle's Medium.

21. The method of claim 1 wherein said immersion is accomplished at a starting temperature of about 20° C. and then, lowering said temperature to about −6° C.

22. The method of claim 21 wherein said lowering is accomplished at a rate of about −10° C./minute.

23. The method of claim 1 wherein said seeding in step (b) is accomplished at a temperature of about −6° C. to about −8° C.

24. The method of claim 1 wherein said cryopreserved tissue is stored at a temperature of at least about −70° C.

25. A method for cryopreserving a harvested mammalian skin or cultured skin or cornea equivalent, comprising:

(a) immersing said tissue in a cryoprotectant solution and agitating said cryoprotectant solution and said immersed tissue to achieve effective penetration of the cryoprotectant solution into said tissue;

(b) lowering the temperature sufficient to achieve ice seeding and for a time sufficient to allow for physical and biological equilibration of said cryoprotectant solution in said tissue;

(c) seeding extracellular ice in said cryoprotectant solution at a temperature of about −6° C. or less; and, (d) cooling said cryoprotectant solution and said tissue at a rate of about −0.3° C. per minute or less to achieve a cryopreserved tissue.

26. The method of claim 25 wherein said cryopreserved tissue is stored at a temperature of at least about −70° C.

27. The method of claim 25 wherein said immersion in step (a) is accomplished at a starting temperature of about 20° C.

28. The method of claim 25 wherein said temperature in step (b) is lowered to about −6° C.

29. The method of claim 25 wherein said lowering of said temperature in step (b) is accomplished at a rate of about −10° C./minute.

30. The method of claim 25 wherein said cultured tissue equivalent is selected from the group consisting of cultured epidermal equivalent, cultured dermal equivalent, and cultured cornea equivalent.

31. The method of claim of claim 25 wherein said cryoprotectant solution is 1.5M to 2.5M glycerol in Dulbecco's Modified Eagles's Medium (DMEM).

32. The method of claim 25, further comprising thawing said cryopreserved tissue, wherein said tissue is thawed in about 1 to about 3 minutes.

* * * * *